United States Patent [19]
Ingrain et al.

[11] Patent Number: 5,343,758
[45] Date of Patent: Sep. 6, 1994

[54] METHOD AND APPARATUS FOR MEASURING GAS FLOW

[75] Inventors: Dominique Ingrain, Villeneuve la Garenne, France; Tapan Bose; Jean-Marie Saint-Arnaud, both of Trois Rivieres, Canada

[73] Assignees: Gaz de France, France; Universite du Quebec àTrois Rivieres, Canada

[21] Appl. No.: 998,591

[22] Filed: Dec. 30, 1992

[30] Foreign Application Priority Data

Dec. 30, 1991 [FR] France .................. 91 16324

[51] Int. Cl.$^5$ ............................ G01F 15/04
[52] U.S. Cl. ................... 73/861.02; 73/30.04
[58] Field of Search ............... 673/23.01, 19.01, 19.04, 673/61.44; 73/861.02, 861.03, 861.04, 30.04

[56] References Cited

U.S. PATENT DOCUMENTS

| | | | |
|---|---|---|---|
| 3,635,084 | 1/1972 | Lamphere et al. | |
| 4,390,956 | 6/1983 | Cornforth et al. | 73/861.03 |
| 4,419,898 | 12/1983 | Zanker et al. | 73/861.02 |
| 4,441,362 | 4/1984 | Carlson | 73/61.44 |
| 4,527,600 | 7/1985 | Fisher et al. | |
| 4,663,977 | 5/1987 | Vander Heyden | |
| 4,829,449 | 5/1989 | Polesnak | 73/861.03 |
| 4,835,456 | 5/1989 | Liu et al. | 73/861.02 |

*Primary Examiner*—Herbert Goldstein
*Attorney, Agent, or Firm*—Bacon & Thomas

[57] ABSTRACT

A method and apparatus for measuring the gaseous flow of a fluid flowing along a duct, the apparatus comprises a processing and control unit connected firstly to a flow rate measuring device which delivers data representative of the flow rate Qm of the gas under the conditions of temperature Tm and pressure Pm that are determined by temperature and pressure sensors disposed in said duct, and secondly to a unit for determining the compressibility factor Zm, which unit delivers data representative of the dielectric constant $\epsilon$ of the gas flowing in the duct, so as to enable the flow rate Q of the gas to be determined as reduced to predefined reference conditions of temperature To, pressure Po, and compressibility factor Zo. The data representative of the dielectric constant of the gas is obtained by a capacitive transducer constituted by a cylindrical capacitor placed under the same thermodynamic conditions as applied to the flow of gas.

13 Claims, 5 Drawing Sheets

METHOD AND APPARATUS FOR MEASURING GAS FLOW

The present invention relates to a method of measuring gas flow in ducts for transporting gas and also to a flow meter for implementing the method.

BACKGROUND OF THE INVENTION

Under normal conditions, gas flow measurement makes use not only of knowledge concerning the temperature T and the pressure P, but also of two other magnitudes, namely the volume flow rate as measured at the temperature T and the pressure P, and the compressibility factor Z or the density $\rho$, which are thermodynamic magnitudes depending on the pressure, the temperature, and the composition of the gas.

Although volume flow rate is easily measured with known uncertainty that is linked directly to the means implemented, be they mechanical means such as spinner meters or piston meters, for example, or be they static means such as diaphragm flow meters or ultrasonic flow meters, in particular, the compressibility factor nevertheless remains a magnitude that is difficult to define and to measure.

Calculation of the compressibility factor requires state equations to be used that are not valid in high pressure domains (greater than 120 bar) and low temperature domains (less than $-8°$ C.), and it is generally measured by means of density sensors that give results that are expressed as discrete values (chromatographic analysis requires a period of 15 minutes to 20 minutes per test).

With a fuel gas, where the composition of the gas varies as do the values of pressure and temperature required in calculating the compressibility factor Z, non-negligible volume errors arise and can give rise to disputes or to disagreements between vendors and purchasers, particularly when it is necessary to reduce the measured volumes to normal conditions of pressure and temperature which may be defined by a local or a national authority or which may merely be defined by an industrial customer, for example.

An object of the present invention is to implement a method of measuring the characteristics of a such as pressure, temperature, and compressibility factor so as to enable the flow rate of the gas to be transmitted to a remote point without requiring human intervention, with only maintenance and inspection requiring limited use of an operator.

SUMMARY OF THE INVENTION

These objects are achieved by a method of measuring the gas flow of a fluid flowing along a duct, the method comprising the following steps:
a) measuring the temperature Tm and the pressure Pm of said gas under its flow conditions, by means of temperature and pressure sensors disposed in the duct;
b) determining the flow rate Qm of said gas under its flow conditions by means of a flow measuring device;
c) determining the dielectric constant $\epsilon$ of the gas under its flow conditions, by measuring the capacitance of a capacitive transducer through which the gas passes, the capacitance in vacuo of said component having previously been established by measurements performed in vacuo;
d) calculating the compressibility factor by means of a processing and control unit on the basis of the determined dielectric constant $\epsilon$ of the gas and of the measured temperature and pressure Tin, Pro, using the following equation:

$$Zm = \frac{Pm}{RTm}\left[\frac{A_\epsilon}{CM} + \frac{B_\epsilon}{A_\epsilon} + \frac{C_\epsilon CM}{A_\epsilon^2} - \frac{B_\epsilon^2 CM}{A_\epsilon^3}\right]$$

or $$Zm = \frac{Pm}{RTm}\left[\frac{A_\epsilon}{CM} + \frac{B_\epsilon}{A_\epsilon}\right]$$

or $$Zm = \left(\frac{Pm}{RTm}\right)\left[\frac{\epsilon + 2}{\epsilon - 1}\right](A_\epsilon)$$

with:

$$CM = \frac{\epsilon - 1}{\epsilon + 2}$$

R being the perfect gas constant and $A_\epsilon$, $B_\epsilon$, and $C_\epsilon$ being coefficients depending in determined manner on the composition of the gas; and e) calculating the gas flow rate Q along the duct as reduced to predetermined reference conditions of temperature To, pressure Po, and compressibility factor Zo in the processing and control unit, using the following equation:

$$Q = Qm(Pm/Po)(To/Tm)(Zo/Zm).$$

This method may be implemented by means of a gas flow measurement device for use with a fluid flowing along a duct, the device including a processing and control unit connected firstly to the flow measuring device which delivers data representative of the flow rate Qm of the gas under conditions of temperature Tm and pressure Pm as determined by temperature and pressure sensors disposed in said duct, and secondly to a unit for determining the compressibility factor Zm which provides, in particular, data representative of the dielectric constant of the gas flowing along the duct, thereby enabling the flow rate of the gas Q to be determined as reduced to predefined reference conditions of temperature To, of pressure Po, and of compressibility factor Zo.

The dielectric constant of the gas is preferably obtained from a capacitive transducer constituted by a cylindrical capacitor, thereby minimizing the turbulence that exists in the flow of the gas along the duct, which transducer is placed in the same thermodynamic conditions as apply to the flow of gas.

Advantageously, the flow measuring device associated with the unit for measuring the compressibility factor is constituted by an ultrasonic flow meter.

The processing and control unit includes analog means for evaluating the dielectric constant of the gas, a micro-controller circuit for determining parameters characteristic of the gas on the basis of said evaluation and on the basis of pressure, temperature, and flow measurements performed on the gas; an input and display unit for displaying these parameters at the request of an operator; and interface circuits for remote transmission of said parameters.

According to a preferred feature, the analog means includes a bridge circuit having the capacitive transducer constituting a first branch thereof, having a second branch adjacent to the first and including a reference capacitor in parallel with a capacitor in series with a digitally controlled attenuator, and having branches opposite to the first and second branches provided by respective opposite-phase alternating signal generators, with balance being achieved when a detector placed at the junction between the first and second branches delivers a null output after a variation of the attenuator value under the control of the processing and control unit.

In a first embodiment of the measurement device of the invention, the capacitive transducer is placed in parallel outside the duct in the circuit of pipework fed with gas flowing along said duct and taken from a point upstream from the capacitive transducer, and an insulating case provides thermal isolation for the assembly so as to ensure that the capacitive transducer is under thermodynamic conditions that are identical to those of the gas, in particular with respect to temperature and pressure.

In another embodiment of the meter of the invention, the capacitive transducer is placed in parallel inside the duct and has the gas flowing along said duct passing though it as conveyed by pipework fed from upstream of the capacitive transducer.

Finally, in yet another embodiment, the said capacitive transducer is placed in an enclosure disposed inside the duct and filled with the gas flowing along said duct as fed by pipework fed from upstream of the capacitive transducer.

BRIEF DESCRIPTION OF THE DRAWINGS

Embodiments of the invention are described by way of example with reference to the accompanying drawings, in which.

DETAILED DESCRIPTION

In the past, flow rate has been measured by well known techniques such as spinner meters or piston meters. However, because of the number of moving parts they contain, such devices do not always guarantee the longevity required by certain gas installations. That is why use is now being made more and more frequently of physical phenomena related to the speed of flow of gases through devices such as vortex meters which make use of the fluid eddies created by an obstacle placed in the flow, or such as ultrasound meters like that shown in FIG. 1 which are based on measuring the propagation speed of ultrasound waves through the gas.

Figure 1:
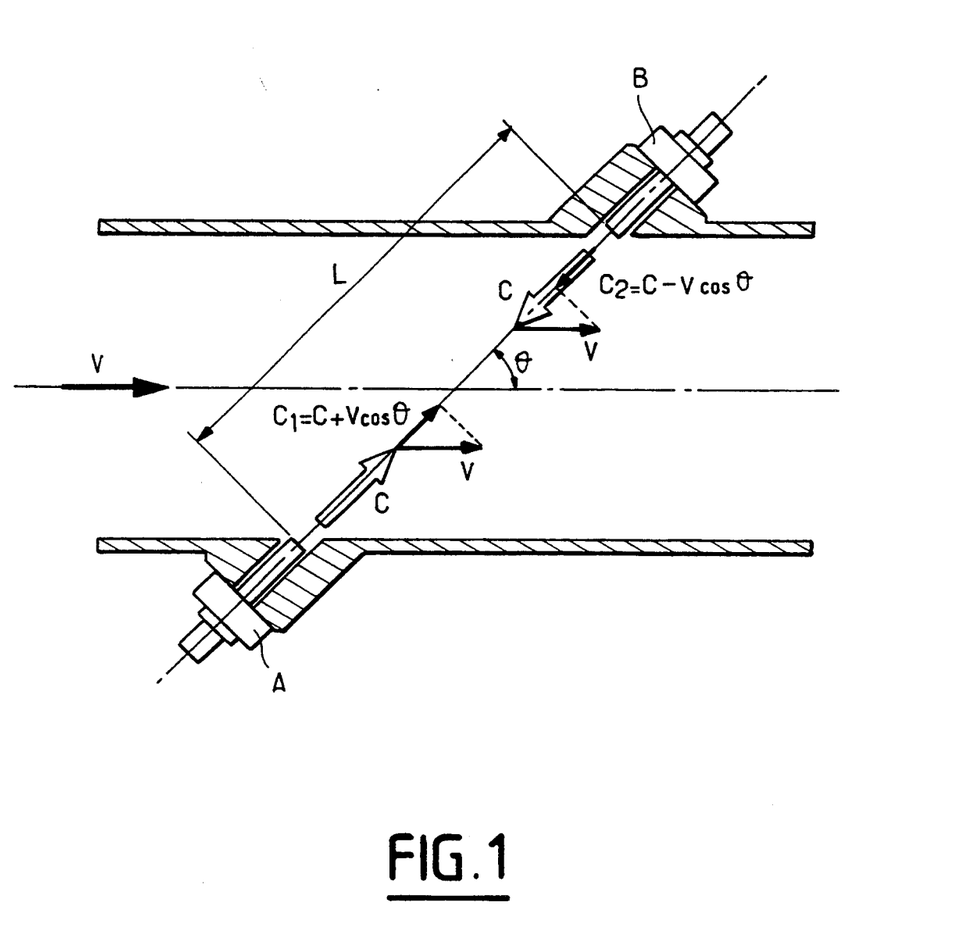
FIG. 1 shows a conventional device for measuring the flow speed of a gas flowing along pipeduct.

This flow meter takes advantage of the variation in the apparent speed of sound as measured in a fluid by means of transducers with variation in the flow speed of the fluid. More exactly, the difference is measured between the propagation times required by the sound in each of two directions between two emitting and receiving probes A and B placed on either side of the duct at a distance L apart, the axes of the probes being at an angle 0 with the axis of said duct, and thus with the axis of the flow.

The travel times $T_{AB}$ and $T_{BA}$ therefore enable $\Delta T$ to be calculated, i.e.:

$$\Delta T = 2VL\cos(\theta)/[c^2 - V^2\cos^2(\theta)]$$

and putting $D = L\sin(\theta)$ the flow speed of the fluid is approximately:

$$V \simeq \frac{c^2 \Delta T}{2D} \tan(\theta)$$

where:
V = the flow speed of the gas;
D = the diameter of the pipeduct;
c = the propagation speed of sound in the gas.

The signals emitted may be wavetrains or pulses, where pulses make it possible to achieve greater accuracy. For even greater accuracy, the so-called three chord method is used, i.e. measurements are performed at various points across the section of the pipeduct since fluid speeds are not uniform.

The integration times required are 40 s for speeds greater than 10 m/s, 100 s for speeds less than 10 m/s, and 340 s for speed less than 2 m/s. The accuracy of such a system is 0.25% between 2% and 10% of full scale and 0.15% above 10% full scale with a probability of 95%. In addition, the absence of any moving part imparts very long life to the device which co-operates perfectly with the unit for measuring the compressibility factor Z which is likewise a totally static device, now described with reference to FIG. 2.

Figure 2:
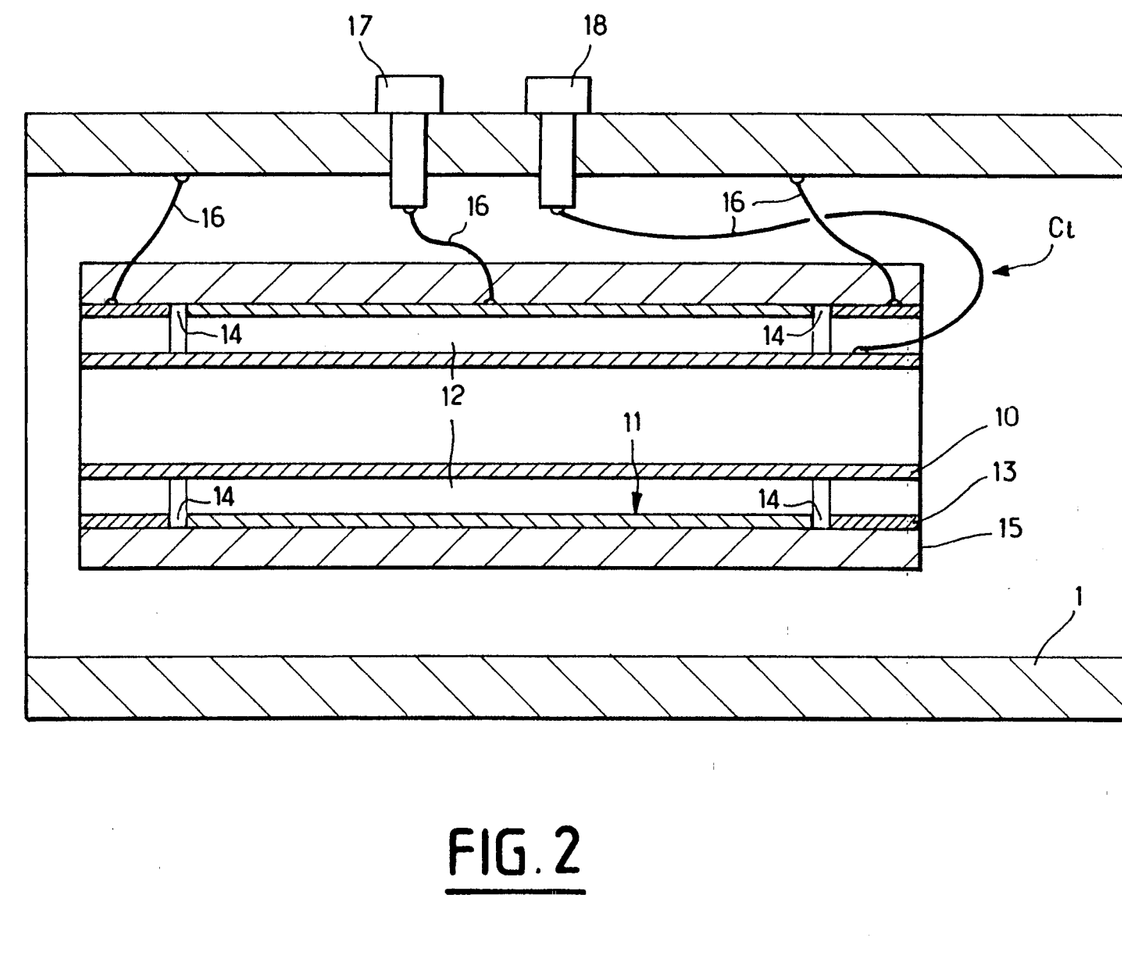
FIG. 2 is a simplified representation of a capacitive transducer used for determining the dielectric constant of the gas in accordance with the invention.

The device for measuring the compressibility factor relies on determining the dielectric constant e of the gas flowing along a duct 1 in which the gas flow rate is to be determined. To do this, the device comprises a capacitor transducer Ct and a reference capacitor Cref.

The capacitive transducer Ct is a cylindrical capacitor so as to minimize turbulence and it comprises a cylindrical inner first electrode 10 having a diameter and a length that are determined and a likewise cylindrical outer second electrode 11 which is concentric about the first but lies outside it, i.e. its greater diameter serves to leave an empty space 12 of annular section between the two electrodes.

The outer electrode 11 is perceptibly shorter than the inner electrode 10, and at each of its ends it is provided with a third electrode 13 disposed in line therewith and separated therefrom by a gap 14, the overall length thus being built out to that of the inner electrode 10. The outer electrode 11 and the third electrode 13 which acts as a guard electrode are in contact with an outer cylinder 15 made of insulating material, while the various electrodes are made of a conductive material, e.g. a metal.

Connection wires 16 serve to connect the electrodes 10, 11, and 13 to an electronic control device (not shown) via terminals 17 and 18 mounted on the duct 1. The terminal 17 is connected, for example, to the outer electrode 11 while the terminal 18 is connected to the inner electrode 10, with the guard element 13 being directly connected to the duct 1. Typically, the capacitor transducer is 300 mm long and has a diameter of 100 min. The outside diameter of the inner electrode is 60 mm and the inside diameter of the outer electrode is 75 min. The assembly has a capacitance in vacuo of 100 pF and it may reach 105 pF at a pressure of 60 bar. The reference capacitor Cref also has a capacitance of 100 pF that is stable to within plus or minus 0.001 pF. Naturally, these values are given merely by way of example and they are not limiting, since they depend in particular on the dimensions of the duct.

Figure 3:
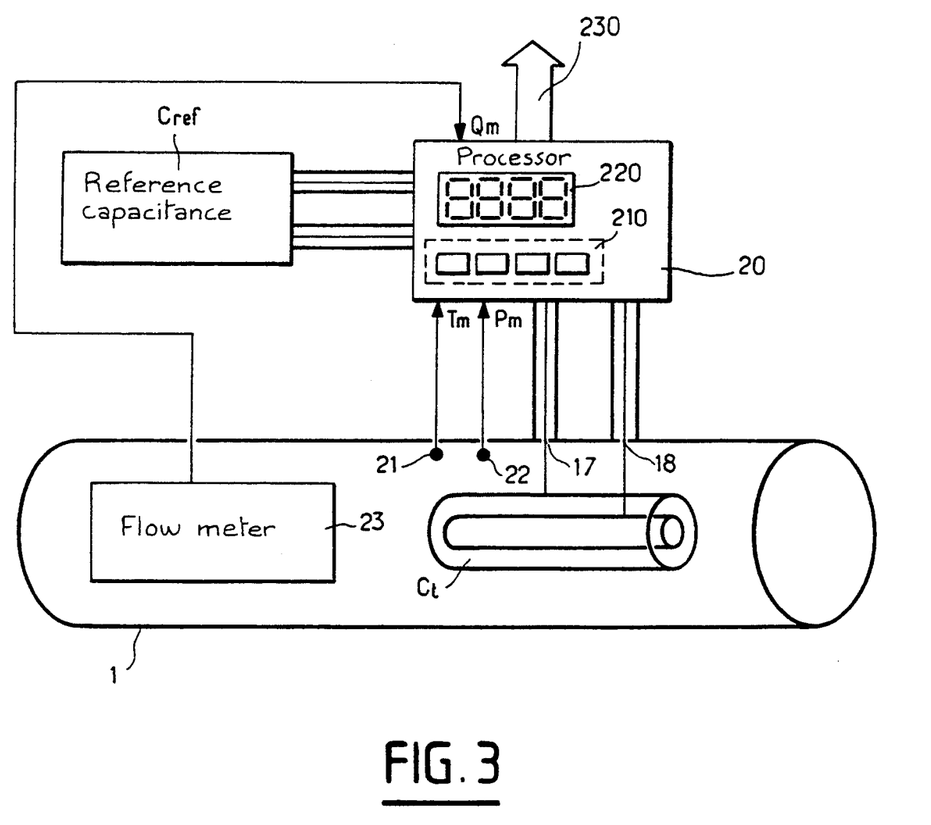
FIG. 3 is an overall view of the device or meter for measuring gas flow in accordance with the invention.

FIG. 3 is an overall view of a device of the invention for measuring gas flow along a duct 1. The device is organized around a processing and controlling central unit 20 which receives various data from the duct 1 and which delivers and displays various results after measurement and possibly after calculation.

There are four main kinds of data that are received: the temperature of the fluid flowing along the duct 1, said temperature being measured, for example, by a temperature gauge 21 disposed in said duct; the pressure of the fluid as determined by means of a pressure gauge 22; the fluid flow under the thermodynamic conditions that exist at the moment the measurement is performed and as determined by means of one of the above-defined conventional devices, and in particular an ultrasound flow meter 23; and finally the dielectric constant of the gas flowing along the duct 1 as obtained by the compressibility factor measuring device which comprises the capacitive transducer Ct and the reference transducer Cref.

Using these various data, the processing and control unit 20 determines various parameters including the density 13 and the compressibility factor Z, and it then calculates the gas flow reduced to predetermined thermodynamic conditions which may be so-called "normal" conditions:

(T=273.15K and P=101325 Pa)

or else so-called "standard" conditions:

(T=288.15K and P=101325 Pa)

or else any other previously defined reference conditions that may depend on special standardization or on a particular request.

A keypad 210 on the computer unit 20 enables data or parameters to be selected so that during maintenance or inspection operations an operator can display them on the display device 220 of said unit 20. All of the measurement or calculation results are made available for further use in digital form on a bus 230 of the unit 20.

Figure 4:
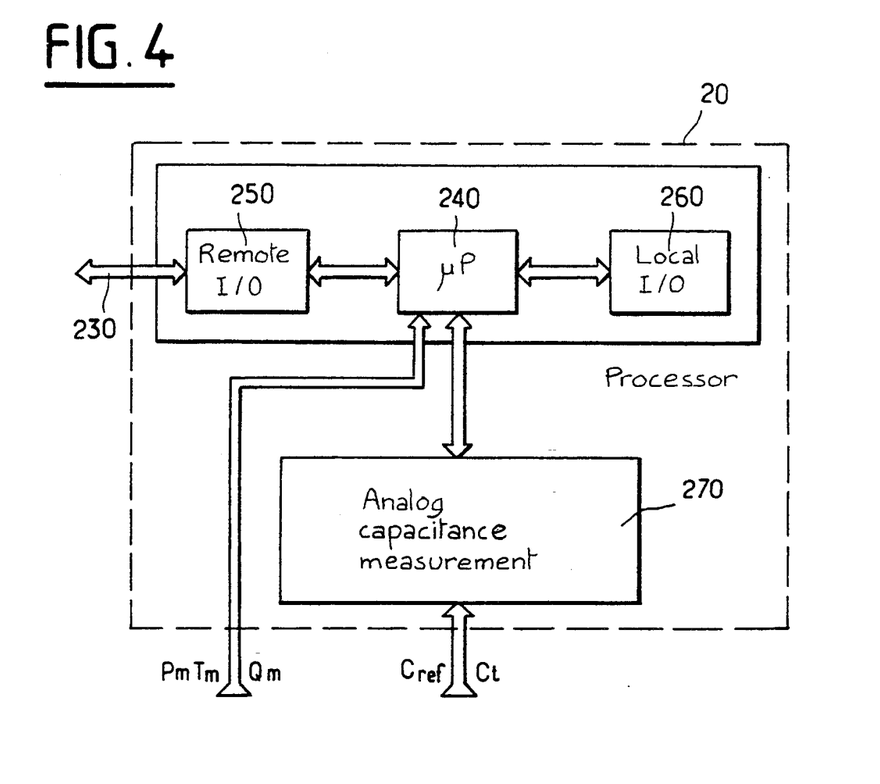
FIG. 4 is a simplified diagram of a processing and control computer unit for the measuring device of the invention.

FIGS. 3 and 4 show in greater detail the architecture of the processing and control computer unit 20. This unit is organized around a microcontroller 240 which may advantageously be constituted by a conventional microprocessor with its associated program and data memories, interface circuits 25 enabling links to be established with the outside via the bus 230, thus enabling various measured or calculated parameters to be read remotely, an input and display unit 260 for displaying such parameters to an operator, if any, and above all analog means 270 for measuring the capacitance of the capacitive transducer Ct.

Figure 5:
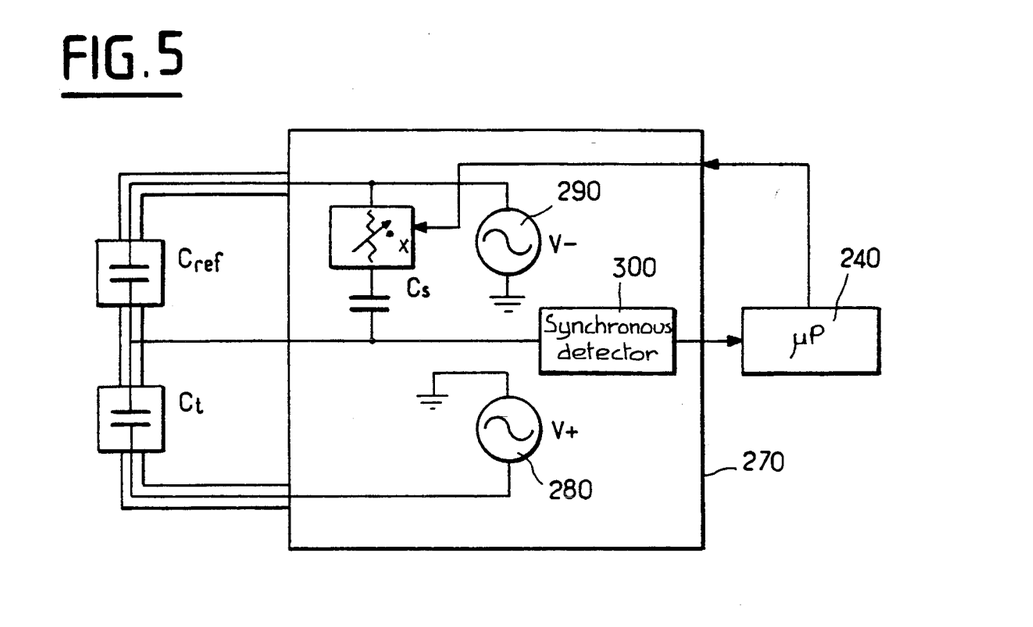
FIG. 5 shows the architecture of the analog unit for determining the dielectric constant of the gas flowing through the capacitive transducer of FIG. 2.

As shown in FIG. 5, the analog means 270 is connected firstly to the reference capacitor Cref and to the capacitive transducer Tc, and secondly to the microcontroller 240. Together with the two capacitors Ct and Cref it forms a capacitance bridge whose balance is sought by a digitally controlled attenuator X. A first branch of the bridge comprises the capacitance to be determined Ct and a first AC generator 280 is connected in the opposite branch. A second branch of the bridge, adjacent to the first, comprises a parallel connection of the reference capacitance Cref and of a capacitance Cs connected in series with the digitally controlled attenuator X. A second AC generator 290 in antiphase to the first is disposed in the opposite branch. Finally, a synchronous detector 300 connected to the junction between the first and second branches serves to evaluate the voltage at this point and thus to determine the value of the capacitance Ct when said voltage is null, i.e. when the bridge established in this way is in balance. Balance is obtained by varying the value of the attenuator X, with such variation being under the control of the microcontroller 240.

At balance, the voltage across the terminals of the detector is null and:

$$Ct = Cref + XCs$$

The dielectric constant $\epsilon$ is then easily determined by taking the ratio of said capacitance Ct and a capacitance Co that corresponds to the capacitance presented by the capacitive transducer in vacuo, and which is previously determined, i.e.:

$$\epsilon = Ct/Co$$

The compressibility factor is given by the following equation:

$$Z = P/\rho RT$$

where P is pressure, $\rho$ is molar density, R is the molar perfect gas constant also known as the universal gas constant, and T is absolute temperature.

$\rho$ may be determined using the Clausius-Mossotti equation:

$$\frac{(\epsilon - 1)}{(\epsilon + 2)} \frac{1}{\rho} = A_\epsilon + B_\epsilon \rho + C_\epsilon \rho^2 + \ldots$$

where $\epsilon$ is the dielectric constant of the gas, and $A_\epsilon$, $B_\epsilon$, and $C_\epsilon$ are known coefficients depending on the composition of the gas and on temperature. (For example see the article by A. D. Buckingham, R. H. Cole, and H. Sutter published in the Journal of Chemical Physics, Jun. 1, 1970, Vol. 52, No. 11, page 5960.)

By combining the last two equations, the measured compressibility factor is obtained:

$$Zm = \frac{Pm}{RTm}\left[\frac{A\epsilon}{CM} + \frac{B\epsilon}{A\epsilon} + \frac{C\epsilon CM}{A\epsilon^2} - \frac{B\epsilon^2 CM}{A\epsilon^3}\right]$$

with:

$$CM = \frac{\epsilon - 1}{\epsilon + 2}$$

It should be observed that by limiting the Clausius-Mossotti equation to the second order, the following expression is obtained for Z:

$$Zm = \frac{Pm}{RTm}\left[\frac{A_\epsilon}{CM} + \frac{B_\epsilon}{A_\epsilon}\right]$$

with:

$$CM = \frac{\epsilon - 1}{\epsilon + 2}$$

and by reducing it to the first order:

$$Zm = \frac{Pm}{RTm}\frac{A_\epsilon}{CM} = \frac{Pm}{RTm}\left[\frac{\epsilon + 2}{\epsilon - 1}\right]A_\epsilon$$

This first order approximately is perfectly satisfactory when operating at pressures of less than 100 bar and providing $A_\epsilon$ has been previously determined, such that measuring $\epsilon$, Pm and Tm then enable Zm under the gas flow conditions to be obtained very simply. These flow conditions vary in non-negligible manner in operation, and to facilitate transactions between vendors and purchasers and to keep account of various different reference conditions mentioned above, it is necessary to reduce these measurement conditions to reference thermo-dynamic conditions, i.e. to apply the following correction coefficient:

$$K=(Pm/Po)(Zo/Zm)(To/Tm)$$

where:
Tm is the temperature measured under the gas flow conditions by the temperature gauge 21;
Pm is the pressure measured under the gas flow conditions by the pressure gauge 22;
Zm is the compressibility factor under the gas flow conditions as calculated from $\epsilon$, Tm, and Tm; and
To, Po, are the reference temperature and pressure, and Zo≃1.

The flow rate provided by the gas flow measuring device of the invention is then equal to: Q=KQm, where Qm is the flow rate measured under the flow conditions of the gas by the flow measuring device 23.

It should be observed that using a microcontroller 240 in the computer unit 20 gives access to all of the parameters that are involved in determining the gas flow. Thus, an operator can call up a display not only of the flow rate Q, but also of the compressibility factor Z, of the density $\rho$, of the capacitance Ct, or of the difference between said capacitance Ct and the reference capacitance Cref. Furthermore, as a function of the measurement device used, the operator may also cause the gas flow speed or the quantity of gas to be displayed as well. These various displayed values naturally require various constants to be previously input into the micro-controller 240, and in particular constants for use in calculating Z.

Figure 6A:
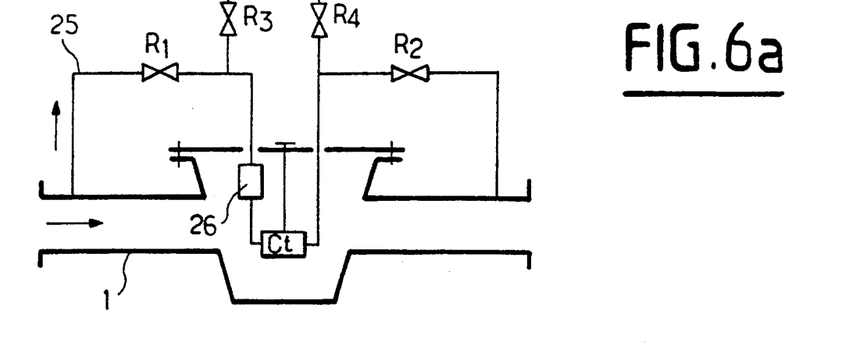
FIGS. 6a to 6c show various positions for placing the unit for measuring compressibility factor in a meter of the invention.
Figure 6B:
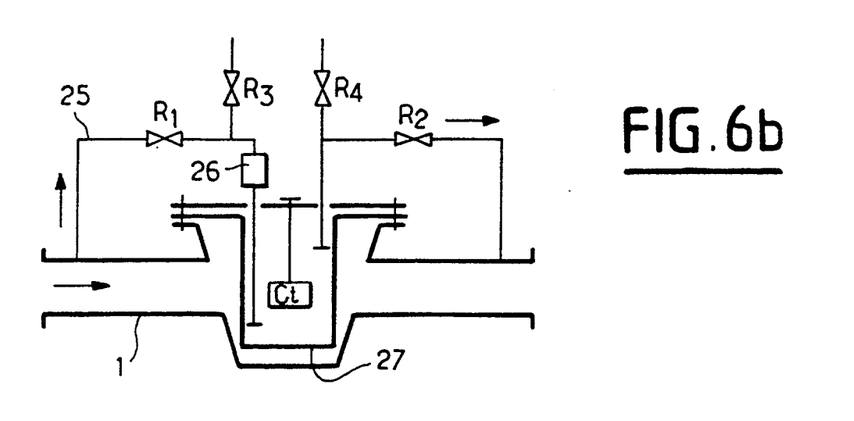
Figure 6C:
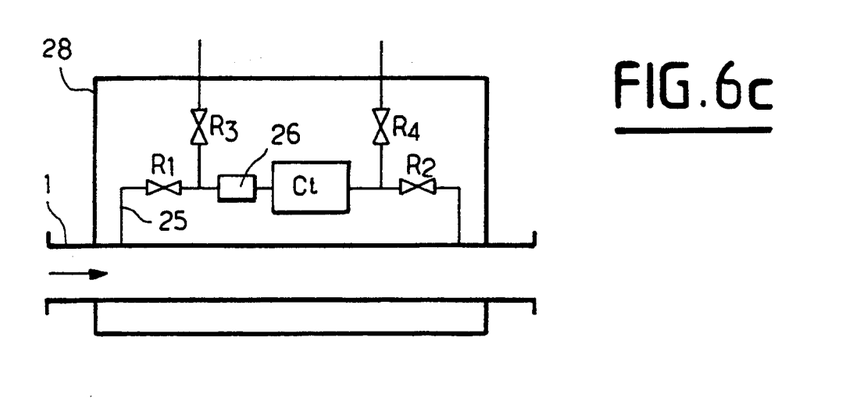

It should be observed that placing the capacitive transducer Ct directly in the duct 1 is not essential, and indeed because of the turbulence in the gas flow, it is preferable to isolate the transducer from the main gas flow while maintaining it under the same thermodynamic conditions. FIGS. 6a to 6c show various possible positions for installing said transducer.

In FIG. 6a, the transducer is placed in the duct 1, and thus at the same temperature T, but it is isolated from the gas flow, being fed via parallel pipework 25 which is itself fed from an upstream point of the duct 1. This avoids turbulence in the system and thereby improves the quality of its measurement.

A filter 26 and valves R1 to R4 placed in the pipework 25 upstream or downstream from the transducer complete this device. In order to reduce these disturbances even further, it is possible to use the configuration shown in FIG. 6b where the transducer is placed in an enclosure 27 placed inside the duct 1. This enclosure is fed with gas via the pipework 25. By reducing the flow speed of the gas by placing the transducer in said enclosure, this device provides greater independence from the disturbances inherent to the gas flowing along the duct.

Nevertheless, both of the above configurations require the pipeduct to be opened in order to receive the transducer. That is why it is also possible to use the configuration shown in FIG. 6c where the transducer is located outside the duct 1, being in parallel therewith. In order to ensure that the thermodynamic conditions in this configuration are the same as those that apply to the gas flowing along the duct, and in particular in order to ensure that the temperature is the same, the branch circuit including the transducer, the pipework 25, and the various filters and valves should be included in an insulating case 28 that also covers a portion of the duct 1. This case 28 thus provides thermal insulation and it enables the capacitive transducer Ct to operate under thermodynamic conditions that are identical to those obtaining in the gas flowing along the duct 1.

Which particular configuration is used, not forgetting other equivalent configurations that the person skilled in the art will be able to devise, depends essentially on the accessibility of the duct or on the type of environment involved, i.e. to what extent it is aggressive. Given the simplicity of these configurations, and the possibility of miniaturizing them, the measuring sensor or device of the invention has a significant advantage over existing devices, in particular in the context of use at high pressure.

Finally, by making use of the dielectric constant of the gas, it is possible to implement a meter that is entirely electronic, thereby facilitating remote monitoring of installations fitted therewith, in particular installations for transporting natural gas.

We claim:
1. A method of measuring the gas flow of a fluid flowing along a duct, the method comprising the following steps:
   a) measuring the temperature Tm and the pressure Pm of said gas under its flow conditions by means of temperature and pressure sensors disposed in the duct;
   b) determining the flow rate Qm of said gas under its flow conditions by means of a flow measuring device;
   c1) causing said gas to flow through a capacitive transducer which has been placed in the same thermodynamic conditions as apply to the flow of gas; measuring the capacitance of the capacitive transducer through which the gas passes, the capaci- tance in vacuo of said transducer having previously been established by measurements performed in vacuo, to determine the dielectric constant $\epsilon$ of the gas under its flow conditions;

d) calculating the compressibility factor by means of a processing and control unit on the basis of the determined dielectric constant $\epsilon$ of the gas and of the measured temperature and pressure Tm, Pm, using the following equation:

$$Zm = \frac{Pm}{RTm} \left[ \frac{A_\epsilon}{CM} + \frac{B_\epsilon}{A_\epsilon} + \frac{C_\epsilon CM}{A_\epsilon^2} - \frac{B_\epsilon^2 CM}{A_\epsilon^2} \right]$$

with:

$$CM = \frac{\epsilon - 1}{\epsilon + 2}$$

R being the perfect gas constant and $A_\epsilon$, $B_\epsilon$, and $C_\epsilon$ being coefficients depending in determined manner on the composition of the gas; and e) calculating the gas flow rate Q along the duct as reduced to predetermined reference conditions of temperature To, pressure To, and compressibility factor Zo in the processing and control unit, using the following equation:

$$Q=Qm(Pm/Po)(To/Tm)(Zo/Zm).$$

2. A method of measuring the gas flow of a fluid flowing along a duct, the method comprising the following steps:

a) measuring the temperature Tm and the pressure Pm of said gas under its flow conditions by means of temperature and pressure sensors disposed in the duct;

b) determining the flow rate Qm of said gas under its flow conditions by means of a flow measuring device;

wherein the method further comprising the following steps:

c1) causing said gas to flow through a capacitive transducer which has been placed in the same thermodynamic conditions as apply to the flow gas;

c2) measuring the capacitance of the capacitive transducer through which the gas passes, the capacitance in vacuo of said component having previously been established by measurements performed in vacuo, to determine the dielectric constant $\epsilon$ of the gas under its flow conditions;

d) calculating the compressibility factor by means of a processing and control unit on the basis of the determined dielectric constant $\epsilon$ of the gas and the measured temperature and pressure Tm, Pm, using the following equation:

$$Zm = \frac{Pm}{RTm} \left[ \frac{A_\epsilon}{CM} + \frac{B_\epsilon}{A_\epsilon} \right]$$

with:

$$CM = \frac{\epsilon - 1}{\epsilon + 2}$$

R being the perfect gas constant $A_\epsilon$ and $B_\epsilon$ being coefficients depending in determined manner on the composition of the gas; and e) calculating the gas flow rate Q along the duct as reduced to predetermined reference conditions of temperature To, pressure Po, and compressibility factor Zo in the processing and control unit, using the following equation:

$$Q=Qm(Pm/Po)(To/Tm)(Zo/Zm).$$

3. A method of measuring the gas flow of a fluid flowing along a duct, the method comprising the following steps:

a) measuring the temperature Tm and the pressure Pm of said gas under its flow conditions by means of temperature and pressure sensors disposed in the duct;

b) determining the flow rate Qm of said gas under its flow conditions by means of a flow measuring device;

wherein the method further comprises the following steps:

c1) causing said gas to flow through a capacitive transducer which has, been placed in the same thermodynamic conditions as apply to the flow of gas;

c2) measuring the capacitance of the capacitive transducer through which the gas passes, the capacitance in vacuo of said component having previously been established by measurements performed in vacuo, to determine the dielectric constant $\epsilon$ of the gas under its flow conditions;

d) calculating the compressibility factor by means of a processing and control unit on the basis of the determined dielectric constant $\epsilon$ of the gas and of the measured temperature and pressure Tm, Pm, using the following equation:

$$Zm = \frac{Pm}{RTm} \left[ \frac{\epsilon + 2}{\epsilon - 1} \right](A_\epsilon)$$

R being the perfect gas constant and $A_\epsilon$ being a coefficient depending in determining manner on the composition of the gas; and e) calculating the gas flow rate Q along the duct as reduced to predetermined reference conditions of temperature To, pressure Po, and compressibility factor Zo in the processing and control unit, using the following equation:

$$Q=Qm(Pm/Po)(To/Tm)(Zo/Zm).$$

4. A method according to any one of claims 1 to 3, further comprising the step of minimizing turbulence by placing a cylindrical capacitor which serves as said capacitive transducer in the flow of gas in the duct.

5. A gas flow measuring device for a fluid flowing in a duct, the device comprising a processing and control unit connected firstly to means for measuring a flow rate Qm of the gas, said flow rate measuring means including temperature Tm and pressure Pm measuring means consisting of temperature and pressure sensors disposed in said duct, and secondly to means for determining a compressibility factor Zm of said gas flowing in the duct, the compressibility determining means in turn including means for measuring the dielectric constant $\epsilon$ of the gas flowing along the duct in order to determine the compressibility of the gas, whereby the gas flow rate Q reduces to predefined reference conditions of temperature To, pressure Po, and compressibility factor Zo.

6. A measurement device according to claim 5, wherein said dielectric constant measuring means comprises a capacitor transducer placed in the same thermodynamic flow conditions as the gas.

7. A measurement device according to claim 6, wherein said capacitive transducer is constituted by a cylindrical capacitor in order to minimize the turbulence that exists in the flow of gas along the duct.

8. A measurement device according to claim 5, wherein said processing and control unit includes analog means for evaluating the dielectric constant $\epsilon$ of the gas; a micro-controller circuit for determining parameters characteristic of the gas on the basis of said evaluation and of the measured pressure, temperature, and flow rate of the gas; an input and display unit for displaying said parameters on request from an operator; and interface circuits for transmitting said parameters remotely.

9. A measurement device according to claim 8, wherein said analog means includes a bridge circuit having the capacitive transducer constituting a first branch thereof and a second branch adjacent to the first and comprising a reference capacitor in parallel with a capacitance connected in series with a digitally controlled attenuator, the branches opposite to the first and second branches each being provided with respective antiphase alternating signal generators, and wherein balance is achieved when a detector placed at the junction between the first and second branches delivers a null voltage after variation in the value of the attenuator under the control of the processing and control unit.

10. A measurement device according to claim 5, wherein said flow measuring device is constituted by an ultrasound flow meter.

11. A measurement device according to claim 5, wherein said capacitive transducer is placed parallel with and outside the duct in a circuit of pipework fed upstream from the capacitor transducer by the gas flowing along said duct, an insulating case ensuring that the assembly is thermally isolated so as to ensure that the capacitive transducer is under thermodynamic conditions identical to those in the gas, and in particular identical temperature conditions.

12. A measurement device according to claim 5, wherein said capacitive transducer is placed in parallel inside the duct and has the gas flowing along said duct flowing therethrough as conveyed by pipework fed upstream from the capacitive transducer.

13. A measurement device according to claim 5, wherein the capacitive transducer is placed in an enclosure placed inside the duct and filled with the gas flowing along the duct, but as delivered by pipework fed upstream from the capacitive transducer.

* * * * *